(12) United States Patent
Lennartz et al.

(10) Patent No.: US 12,426,941 B2
(45) Date of Patent: Sep. 30, 2025

(54) SURGICAL INSTRUMENTS AND SYSTEMS CONFIGURED TO DETECT, ANALYZE, AND/OR DISTINGUISH SMOKE AND STEAM DURING A SURGICAL PROCEDURE

(71) Applicant: Covidien LP, Mansfield, MA (US)

(72) Inventors: Amanda H. Lennartz, Erie, CO (US); Daniel A. Joseph, Golden, CO (US); Jennifer R. McHenry, Denver, CO (US); Cornelia F. Twomey, Longmont, CO (US); Erin E. Wehrly, Longmont, CO (US); Tracy J. Pheneger, Longmont, CO (US); David M. Garrison, Longmont, CO (US); Tyler J. Bagrosky, Arvada, CO (US); Robert H. Wham, Boulder, CO (US); Jing Zhao, Superior, CO (US)

(73) Assignee: Covidien LP, Mansfield, MA (US)

( * ) Notice: Subject to any disclaimer, the term of this patent is extended or adjusted under 35 U.S.C. 154(b) by 495 days.

(21) Appl. No.: 17/161,432

(22) Filed: Jan. 28, 2021

(65) Prior Publication Data

US 2021/0290297 A1    Sep. 23, 2021

Related U.S. Application Data

(60) Provisional application No. 62/990,865, filed on Mar. 20, 2020, provisional application No. 62/992,837, (Continued)

(51) Int. Cl.
*A61B 18/14*    (2006.01)
*A61B 18/00*    (2006.01)
*A61B 34/30*    (2016.01)

(52) U.S. Cl.
CPC ............ *A61B 18/1445* (2013.01); *A61B 2018/00077* (2013.01); *A61B 2018/00773* (2013.01); *A61B 2018/1455* (2013.01); *A61B 34/30* (2016.02)

(58) Field of Classification Search
CPC ........... A61B 18/1442; A61B 18/1445; A61B 18/1447; A61B 2018/1442;
(Continued)

(56) References Cited

U.S. PATENT DOCUMENTS

| 4,502,487 A | 3/1985 | DuBrucq et al. |
| 5,460,182 A | 10/1995 | Goodman et al. |

(Continued)

*Primary Examiner* — Sean W Collins
*Assistant Examiner* — Nora W Rhodes

(57) ABSTRACT

An electrosurgical system includes an end effector assembly and a sensor. The end effector assembly includes first and second jaw members each defining an electrically-conductive tissue-contacting surface. At least one of the first or second jaw members is movable relative to the other between a spaced-apart position and an approximated position for grasping tissue between the tissue-contacting surfaces thereof. The electrically-conductive tissue-contacting surfaces of the first and second jaw members are adapted to connect to a source of electrosurgical energy for conducting energy through tissue grasped therebetween to treat tissue. The sensor is configured to sense at least one property of smoke produced as a result of the conduction of energy through tissue grasped between the electrically-conductive tissue-contacting surfaces.

18 Claims, 11 Drawing Sheets

Related U.S. Application Data filed on Mar. 20, 2020, provisional application No. 62/992,871, filed on Mar. 20, 2020.

(58) Field of Classification Search
CPC ...... A61B 2018/145; A61B 2018/1452; A61B 2018/1455; A61B 2018/1457; A61B 2018/146; A61B 2018/1462
See application file for complete search history.

(56) References Cited

U.S. PATENT DOCUMENTS

| | | |
|---|---|---|
| 5,494,045 A | 2/1996 | Kiviranta et al. |
| 6,030,384 A | 2/2000 | Nezhat |
| 6,071,242 A | 6/2000 | Lin |
| 6,190,353 B1 | 2/2001 | Makower et al. |
| 6,723,092 B2 | 4/2004 | Brown et al. |
| 7,217,268 B2 | 5/2007 | Eggers et al. |
| 7,625,370 B2 | 12/2009 | Hart et al. |
| 7,731,717 B2 | 6/2010 | Odom et al. |
| 7,753,871 B2 | 7/2010 | Mehier |
| 7,776,037 B2 | 8/2010 | Odom |
| 8,216,235 B2 | 7/2012 | Rioux et al. |
| 8,382,754 B2 | 2/2013 | Odom et al. |
| 8,439,913 B2 | 5/2013 | Horner et al. |
| 8,579,892 B2 | 11/2013 | Hoey et al. |
| 8,906,016 B2 | 12/2014 | Boudreaux et al. |
| 9,011,367 B2 | 4/2015 | Humbert et al. |
| 9,149,260 B2 | 10/2015 | Stone et al. |
| 9,173,698 B2 | 11/2015 | Van Lue et al. |
| 9,247,988 B2 | 2/2016 | McKenna et al. |
| 9,375,259 B2 | 6/2016 | Payne et al. |
| 9,420,983 B2 | 8/2016 | Zagorchev et al. |
| 9,603,652 B2 | 3/2017 | Carlton et al. |
| 9,642,665 B2 | 5/2017 | Weinberg et al. |
| 9,693,816 B2 | 7/2017 | Orszulak |
| 9,839,467 B2 | 12/2017 | Harper et al. |
| 9,918,783 B2 | 3/2018 | Horner et al. |
| 10,117,705 B2 | 11/2018 | Chernov et al. |
| 10,130,413 B2 | 11/2018 | Brandt et al. |
| 10,143,533 B2 | 12/2018 | Park |
| 10,188,448 B2 | 1/2019 | Friedrichs |
| 10,245,104 B2 | 4/2019 | McKenna et al. |
| 10,335,226 B2 | 7/2019 | Harper et al. |
| 10,893,899 B2 | 1/2021 | Weber |
| 2002/0128650 A1* | 9/2002 | McClurken ........ A61B 18/1442 606/50 |
| 2002/0177846 A1 | 11/2002 | Mulier et al. |
| 2003/0225324 A1 | 12/2003 | Anderson et al. |
| 2005/0043623 A1 | 2/2005 | Jurvelin et al. |
| 2006/0116572 A1 | 6/2006 | Case |
| 2007/0049920 A1* | 3/2007 | McClurken ............ A61B 18/14 606/34 |
| 2008/0021373 A1 | 1/2008 | Rosati |
| 2009/0028793 A1 | 1/2009 | Neri et al. |
| 2009/0204114 A1 | 8/2009 | Odom |
| 2010/0036374 A1* | 2/2010 | Ward ................ A61B 18/1206 604/23 |
| 2010/0069941 A1 | 3/2010 | Cohen et al. |
| 2010/0152586 A1 | 6/2010 | Grant et al. |
| 2010/0217264 A1 | 8/2010 | Odom et al. |
| 2010/0331838 A1 | 12/2010 | Ibrahim et al. |
| 2011/0009899 A1 | 1/2011 | Picha Muthu et al. |
| 2011/0112570 A1 | 5/2011 | Mannava et al. |
| 2012/0041345 A1 | 2/2012 | Rajamani et al. |
| 2013/0171649 A1 | 7/2013 | Mayr |
| 2013/0281920 A1* | 10/2013 | Hawkins ............ A61B 18/1815 604/26 |
| 2015/0088125 A1 | 3/2015 | Wham |
| 2015/0223868 A1 | 8/2015 | Brandt et al. |
| 2015/0289925 A1* | 10/2015 | Voegele ............ A61B 18/1233 606/51 |
| 2016/0045248 A1 | 2/2016 | Unger et al. |
| 2016/0089198 A1 | 3/2016 | Arya et al. |
| 2016/0135868 A1* | 5/2016 | Joseph ............... A61B 18/1445 606/34 |
| 2016/0174998 A1 | 6/2016 | Lal et al. |
| 2016/0346034 A1 | 12/2016 | Arya et al. |
| 2017/0035929 A1 | 2/2017 | Phillips et al. |
| 2017/0061621 A1 | 3/2017 | Wortman |
| 2017/0079740 A1 | 3/2017 | Hufnagel et al. |
| 2017/0215943 A1 | 8/2017 | Allen, IV |
| 2017/0215944 A1 | 8/2017 | Keffeler |
| 2017/0238991 A1* | 8/2017 | Worrell .................. H05K 1/034 |
| 2017/0252479 A1 | 9/2017 | Ji et al. |
| 2017/0265831 A1 | 9/2017 | Sankaran et al. |
| 2017/0319190 A1 | 11/2017 | Rooks |
| 2017/0372474 A1 | 12/2017 | Behar et al. |
| 2019/0019347 A1 | 1/2019 | Auvray et al. |
| 2019/0057541 A1 | 2/2019 | Li et al. |
| 2019/0083168 A1 | 3/2019 | Wham |
| 2019/0201083 A1* | 7/2019 | Shelton, IV ..... A61B 17/07207 |
| 2019/0201137 A1* | 7/2019 | Shelton, IV ............ G16H 50/20 |
| 2019/0204201 A1* | 7/2019 | Shelton, IV ........... G16H 20/40 |
| 2019/0282296 A1 | 9/2019 | Harper et al. |

\* cited by examiner

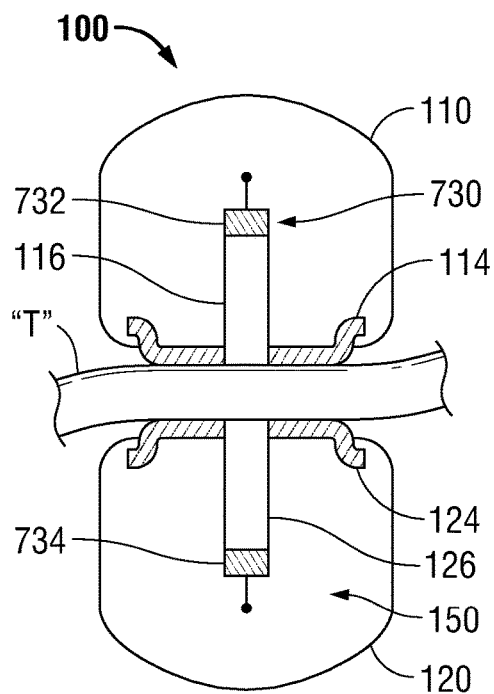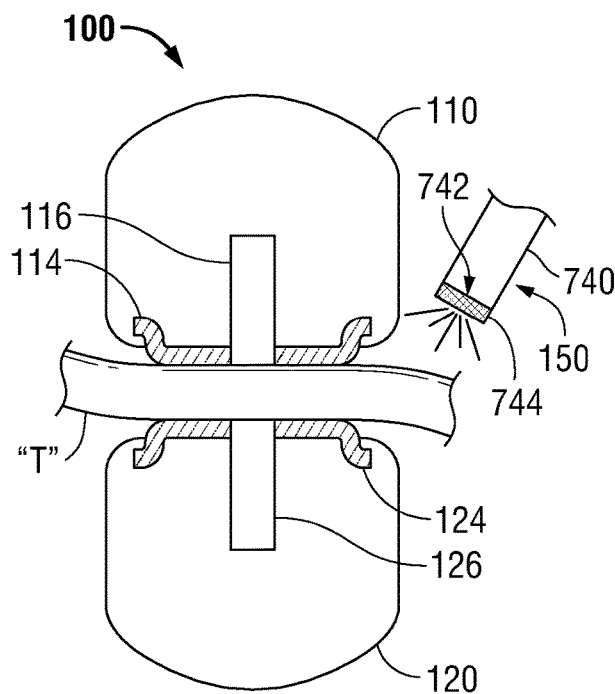
FIG. 8
FIG. 9
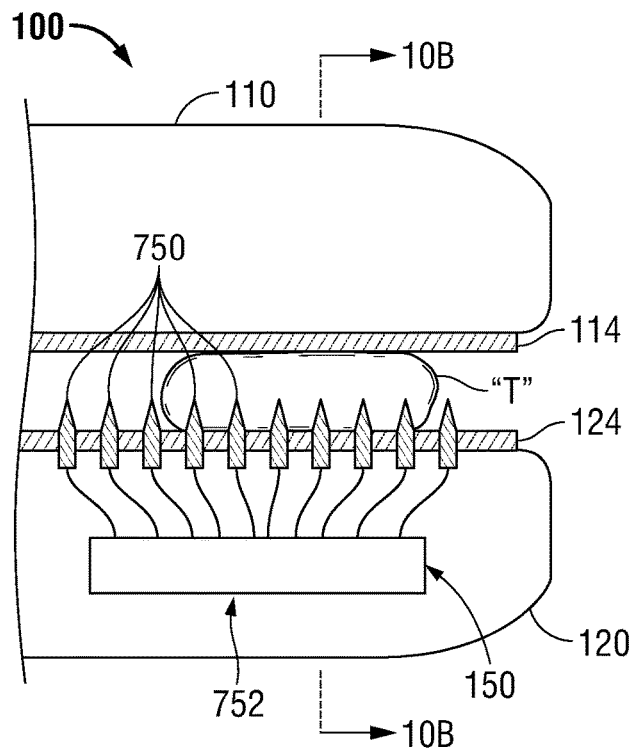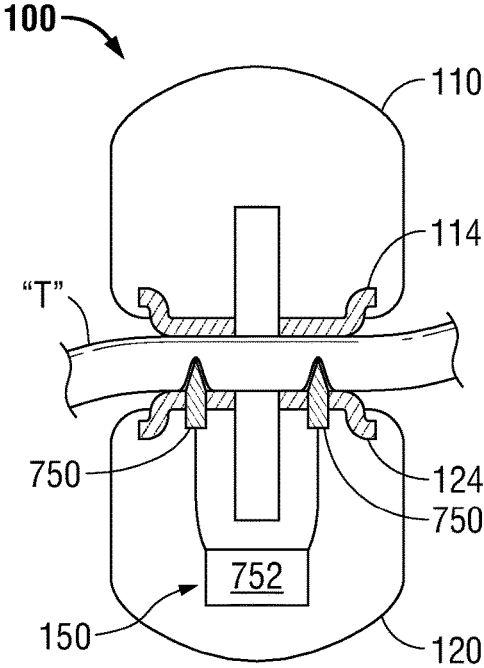
FIG. 10A
FIG. 10B

SURGICAL INSTRUMENTS AND SYSTEMS CONFIGURED TO DETECT, ANALYZE, AND/OR DISTINGUISH SMOKE AND STEAM DURING A SURGICAL PROCEDURE

CROSS-REFERENCE TO RELATED APPLICATIONS

This application claims the benefit of, and priority to, U.S. Provisional Patent Application Nos. 62/992,837, 62/992,865, and 62/992,871, each filed on Mar. 20, 2020, the entire contents of each of which is hereby incorporated herein by reference.

FIELD

The present disclosure relates to surgical instruments and systems, and, more particularly, to energy-based surgical instruments and systems configured to detect, analyze, and/or distinguish smoke and steam during the application of energy to tissue to facilitate tissue treatment.

BACKGROUND

Surgical instruments and methods for energy-based tissue treatment may utilize mechanical clamping action and application of energy, e.g., bipolar electrosurgical energy, to affect hemostasis by heating tissue to treat, e.g., coagulate, cauterize, and/or seal, tissue. Other surgical instruments include an energizable element, e.g., a monopolar electrosurgical element, a thermal element, etc., for energy-based tissue dissection.

SUMMARY

As used herein, the term "distal" refers to the portion that is being described which is farther from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, and/or other variations, up to and including plus or minus 10 percent. Further, any or all of the aspects described herein, to the extent consistent, may be used in conjunction with any or all of the other aspects described herein.

Provided in accordance with aspects of the present disclosure is a surgical system including a surgical instrument configured for insertion into a surgical site, a sensor configured to sense at least one property of smoke at the surgical site, and a surgical generator including a controller and an energy output configured to supply energy to the surgical instrument for application to tissue at the surgical site to treat the tissue. The controller is configured to receive the at least one property and determine at least one parameter of smoke at the surgical site based upon the at least one property. The controller is further configured to control the energy output based upon the at least one parameter and/or provide an output based upon the at least one parameter.

In an aspect of the present disclosure, the sensor includes at least one of: an optical sensor, an electrical sensor, a smell-based sensor, or a chemical sensor.

In another aspect of the present disclosure, the at least one property includes: an optical property, a chemical property, an electrical property, or a smell-based property.

In yet another aspect of the present disclosure, the at least one parameter includes: presence of smoke, presence of a type of smoke particle, an amount of smoke particles, an amount of steam particles, or a ratio of smoke to steam. Additionally or alternatively, the at least one parameter includes: temperature of smoke, density of smoke, or color of smoke.

In still another aspect of the present disclosure, controlling the energy output includes at least one of: starting, modifying, continuing, or stopping the supply of energy to the surgical instrument.

In still yet another aspect of the present disclosure, the controller includes a storage device storing a machine learning algorithm configured to determine the at least one parameter based upon the at least one property.

In another aspect of the present disclosure, the controller is further configured to determine a type of the tissue being treated based upon the at least one parameter. The controller, in such aspects, may further be configured to control the energy output based upon the type of the tissue being treated and/or provide, via the output, an indication of the type of the tissue being treated.

In still another aspect of the present disclosure, the controller is further configured to determine a state of the tissue being treated based upon the at least one parameter. The controller, in such aspects, may further be configured to control the energy output based upon the state of the tissue being treated and/or provide, via the output, an indication of the state of the tissue being treated.

In yet another aspect of the present disclosure, the controller is further configured to determine a status of tissue treatment based upon the at least one parameter. The controller, in such aspects, may further be configured to control the energy output based upon the status of tissue treatment and/or provide, via the output, an indication of the status of the tissue treatment.

In an aspect of the present disclosure, the output includes at least one of: an audible output, a visual output, or a tactile output.

A method of surgery provided in accordance with the present disclosure includes inserting a surgical instrument into a surgical site, supplying energy from a surgical generator to tissue at the surgical site via the surgical instrument to treat the tissue, sensing at least one property of smoke at the surgical site, and determining at least one parameter of smoke at the surgical site based upon the at least one property. The method further includes controlling the supply of energy from the surgical generator based upon the at least one parameter and/or providing an output based upon the at least one parameter.

In an aspect of the present disclosure, sensing the at least one property includes sensing an optical property, a chemical property, an electrical property, or a smell-based property.

In another aspect of the present disclosure, determining the at least one parameter includes determining presence of smoke, presence of a type of smoke particle, an amount of smoke particles, or a ratio of smoke to steam. Additionally or alternatively, determining the at least one parameter includes determining temperature of smoke, density of smoke, or color of smoke.

In still another aspect of the present disclosure, the sensing is performed by a device separate from the surgical instrument, e.g., a surgical camera.

In yet another aspect of the present disclosure, controlling the supply of energy includes at least one of: starting, modifying, continuing, or stopping the supply of energy from the surgical generator to the surgical instrument.

In still yet another aspect of the present disclosure, the at least one parameter is determined using a machine learning algorithm.

In another aspect of the present disclosure, providing the output includes providing at least one of an audible output, a visual output, or a tactile output.

In yet another aspect of the present disclosure, the method further includes determining a type of the tissue being treated based upon the at least one parameter. In such aspects, the method may further include controlling the supply of energy based upon the type of the tissue being treated and/or indicating, via the output, the type of the tissue being treated.

In still another aspect of the present disclosure, the method further includes determining a state of the tissue being treated based upon the at least one parameter. In such aspects, the method may further include controlling the supply of energy based upon the state of the tissue being treated and/or indicating, via the output, the state of the tissue being treated.

In another aspect of the present disclosure, the method further includes determining a status of tissue treatment based upon the at least one parameter. In such aspects, the method may further include controlling the supply of energy based upon the status of tissue treatment and/or indicating, via the output, the status of tissue treatment.

An electrosurgical system provided in accordance with aspects of the present disclosure includes an end effector assembly and a sensor. The end effector assembly includes first and second jaw members each defining an electrically-conductive tissue-contacting surface. At least one of the first or second jaw members is movable relative to the other between a spaced-apart position and an approximated position for grasping tissue between the tissue-contacting surfaces thereof. The electrically-conductive tissue-contacting surfaces of the first and second jaw members are adapted to connect to a source of electrosurgical energy for conducting energy through tissue grasped therebetween to treat tissue. The sensor is configured to sense at least one property of smoke produced as a result of the conduction of energy through tissue grasped between the electrically-conductive tissue-contacting surfaces.

In an aspect of the present disclosure, the sensor is incorporated into the end effector assembly. The sensor, in such aspects, may be disposed on or within one of the first or second jaw members. Alternatively, the sensor may be incorporated into a device separate from the end effector assembly.

The sensor and/or the at least one property may be similar to any of the aspects detailed above or otherwise herein.

In another aspect of the present disclosure, the sensor is further configured to sense at least one property of steam produced as a result of the conduction of energy through tissue grasped between the electrically-conductive tissue-contacting surfaces.

In yet another aspect of the present disclosure, the electrosurgical system further includes a controller. In such aspects, the sensor is configured to communicate the at least one property to the controller. The controller may be configured to determine at least one parameter of smoke produced as a result of the conduction of energy through tissue grasped between the electrically-conductive tissue-contacting surfaces based upon the at least one property, e.g., any of the parameters detailed above or otherwise herein.

In still another aspect of the present disclosure, the controller is configured to determine a type of tissue being treated based upon the at least one property, a state of tissue being treated based upon the at least one parameter, and/or a status of tissue treatment based upon the at least one parameter.

In still yet another aspect of the present disclosure, a housing and a shaft extending distally from the housing are provided. The end effector assembly is disposed at a distal end portion of the shaft in such aspects. A manual actuator, e.g., handle, may be coupled to the housing and configured to move the at least one of the first or second jaw members between the spaced-apart position and the approximated position.

In another aspect of the present disclosure, first and second shaft members pivotably coupled to one another about a pivot are provided. In such aspects, the end effector assembly extends distally from the pivot and the first and second shaft members are movable relative to one another to move the at least one of the first or second jaw members between the spaced-apart position and the approximated position.

In yet another aspect of the present disclosure, a robotic arm is provided wherein the end effector assembly extends distally from the robotic arm.

In another aspect of the present disclosure, the sensor is an optical sensor including a transmitter and a receiver.

In still another aspect of the present disclosure, the sensor includes at least one needle configured to penetrate tissue grasped between the tissue-contacting surfaces of the first and second jaw members.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

FIG. 8 is a transverse, cross-sectional view of the jaw members of the end effector assembly of FIG. 1B shown grasping tissue therebetween and including a sensor mechanism incorporated therein;

FIG. 9 is a transverse, cross-sectional view of the jaw members of the end effector assembly of FIG. 1B shown grasping tissue therebetween and including an external sensor mechanism associated therewith;

FIGS. 10A and 10B are longitudinal and transverse cross-sectional views, respectively, of the jaw members of the end effector assembly of FIG. 1B shown grasping tissue therebetween and including another sensor mechanism incorporated therein.

DETAILED DESCRIPTION

The present disclosure provides energy-based surgical instruments and systems configured to detect, analyze, and/or distinguish smoke and steam during the application of energy to tissue to facilitate tissue treatment. Various exemplary energy-based surgical instruments, systems, and sensor mechanisms are detailed below; however, the aspects and features of the present disclosure are not limited thereto as any other suitable energy-based surgical instruments, systems, and/or sensor mechanisms are also contemplated for use in accordance with the present disclosure.

Figure 1A:
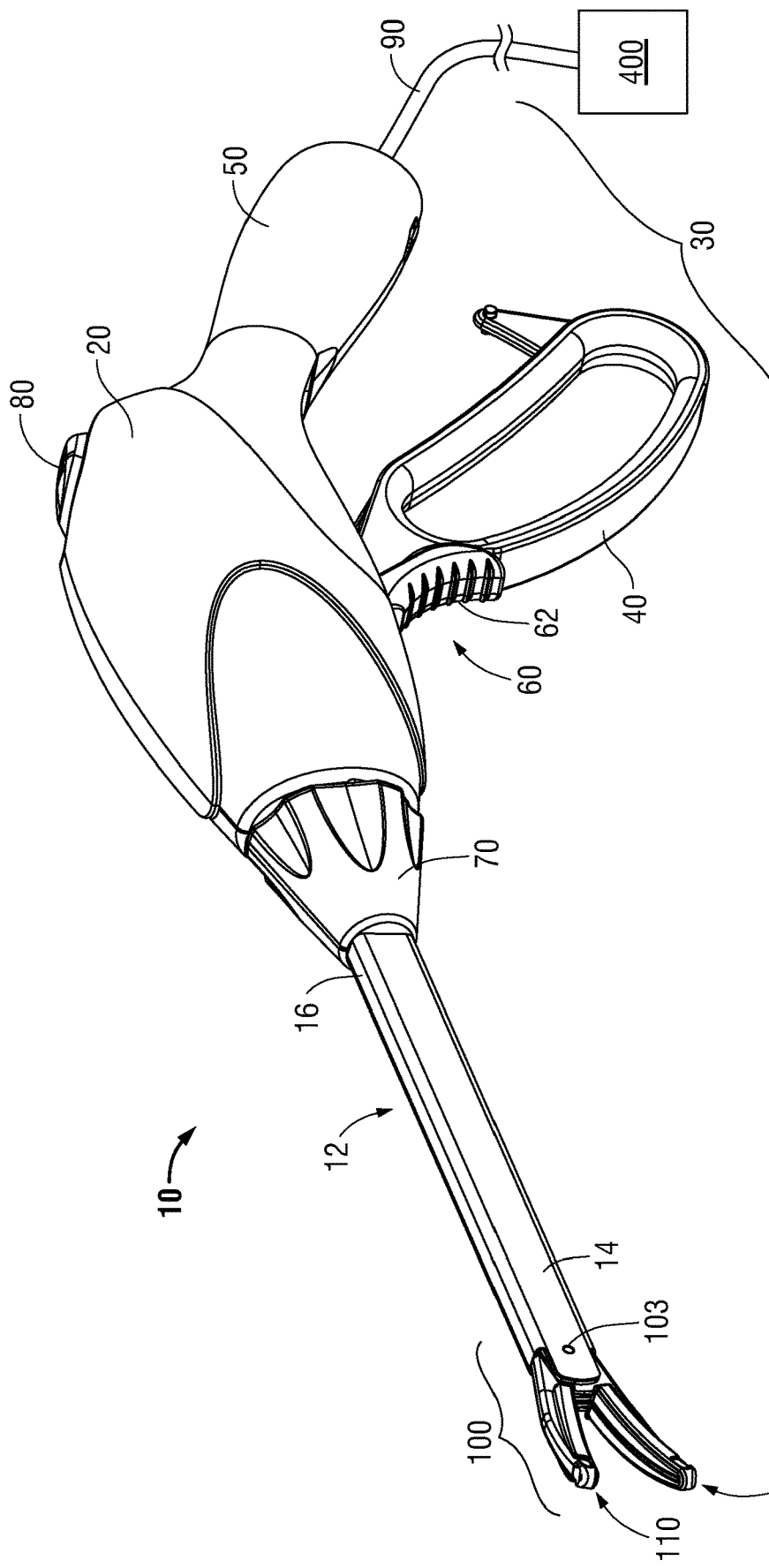
FIG. 1A is a perspective view of a shaft-based electrosurgical forceps provided in accordance with the present disclosure connected to an electrosurgical generator.

Referring to FIG. 1A, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a trigger assembly 60, a rotating assembly 70, an activation switch 80, and an end effector assembly 100. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable 90 that connects forceps 10 to an electrosurgical generator 400. Cable 90 includes a wire (or wires) (not shown) extending therethrough that has sufficient length to extend through shaft 12 in order to provide energy to one or both tissue-contacting surfaces 114, 124 of jaw members 110, 120, respectively, of end effector assembly 100 (see FIGS. 1B and 1C). Activation switch 80 is coupled to tissue-contacting surfaces 114, 124 (FIGS. 1B and 1C) and electrosurgical generator 400 for enabling the selective activation of the supply of energy to jaw members 110, 120 for treating, e.g., sealing, tissue.

Handle assembly 30 of forceps 10 includes a fixed handle 50 and a movable handle 40 (although both handles 40, 50 may move, in embodiments). Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced-apart position (FIG. 1B) and an approximated position (FIG. 1C) to grasp tissue between jaw members 110, 120. As shown in FIG. 1A, movable handle 40 is initially spaced-apart from fixed handle 50 and, correspondingly, jaw members 110, 120 of end effector assembly 100 are disposed in the spaced-apart position. Movable handle 40 is depressible from this initial position to a depressed position corresponding to the approximated position of jaw members 110, 120 (FIG. 1C).

Trigger assembly 60 includes a trigger 62 coupled to housing 20 and movable relative thereto between an un-actuated position and an actuated position. Trigger 62 is operably coupled to a knife 64 (FIG. 1i), so as to actuate knife 64 (FIG. 1B) to cut tissue grasped between jaw members 110, 120 of end effector assembly 100 upon actuation of trigger 62. As an alternative to knife 64, other suitable mechanical, electrical, or electromechanical cutting mechanisms (stationary or movable) are also contemplated.

Figure 1B:
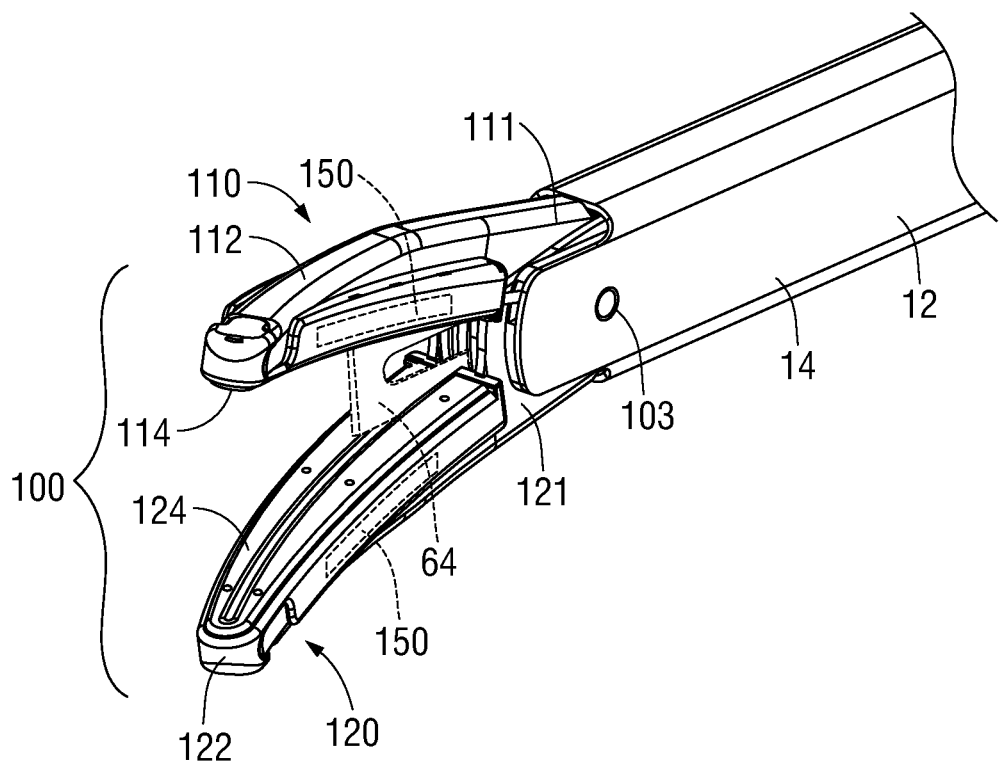
FIG. 1B is a perspective view of a distal end portion of the forceps of FIG. 1A, wherein jaw members of an end effector assembly of the forceps are disposed in a spaced-apart position.
Figure 1C:
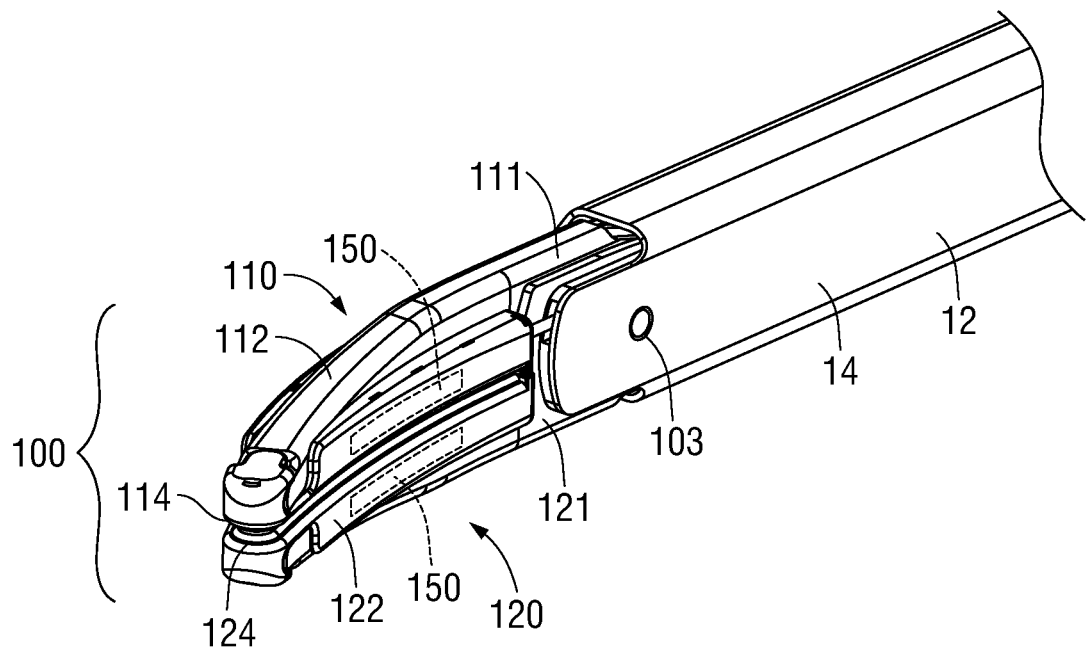
FIG. 1C is a perspective view of the distal end portion of the forceps of FIG. 1A, wherein the jaw members are disposed in an approximated position.
Figure 2A:
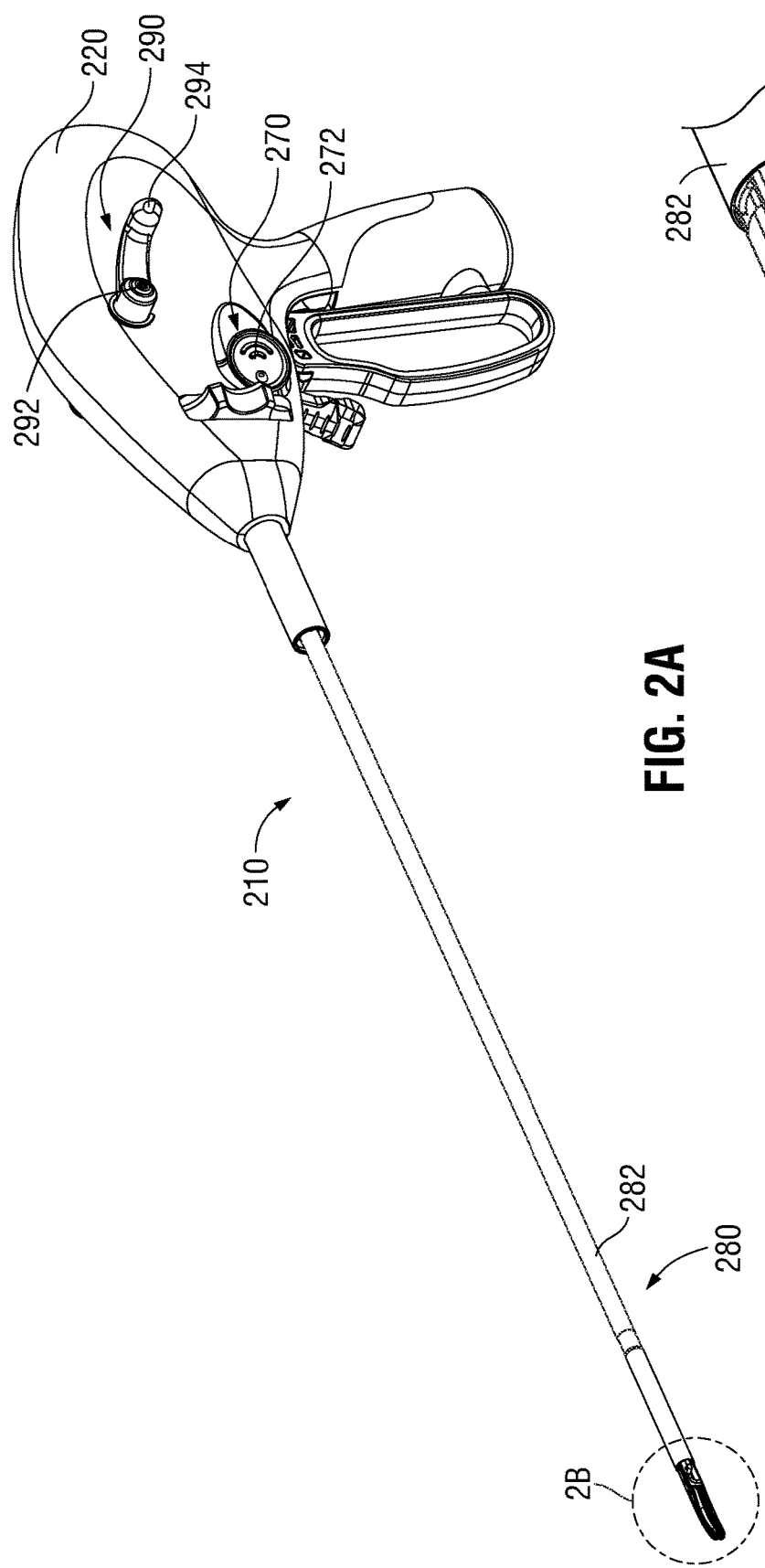
FIG. 2A is a perspective view of a shaft-based multi-function instrument provided in accordance with the present disclosure, with a deployable assembly thereof disposed in a retracted position.
Figure 2B:
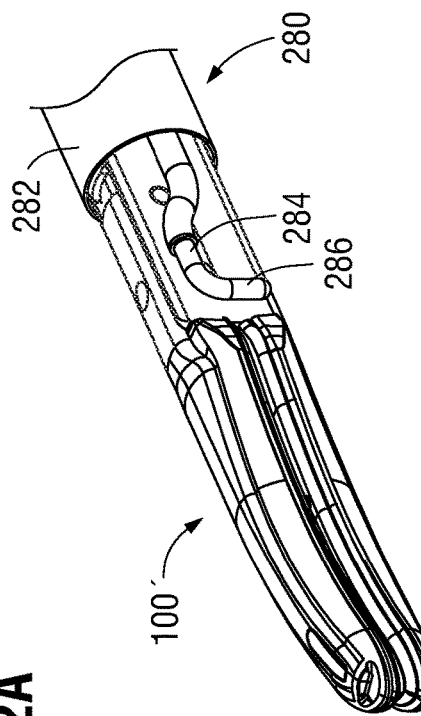
FIG. 2B is an enlarged, perspective view of the area of detail indicated as "2B" in FIG. 2A.
Figure 2C:
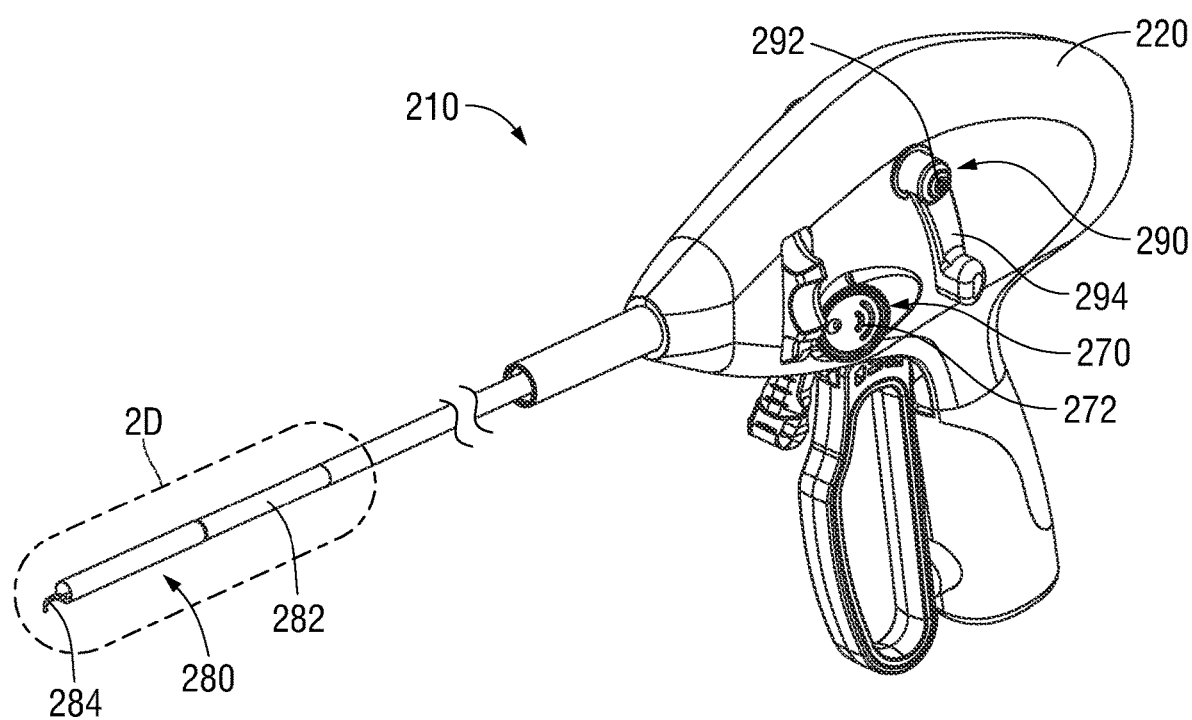
FIG. 2C is a perspective view of the shaft-based multi-function instrument of FIG. 2A with the deployable assembly thereof disposed in an extended position.
Figure 2D:
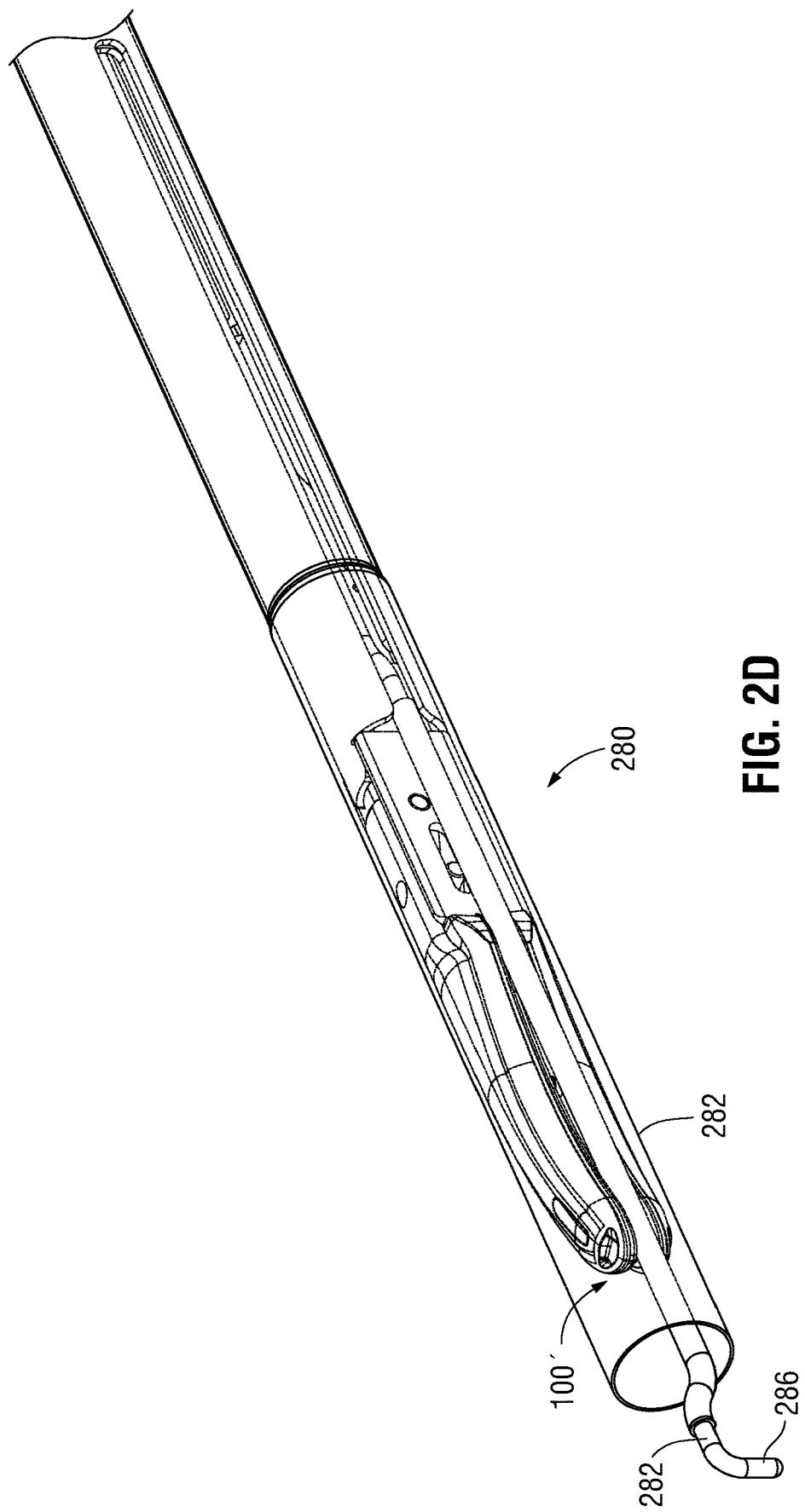
FIG. 2D is an enlarged, perspective view of the area of detail indicated as "2D" in FIG. 2C.

With additional reference to FIGS. 1B and 1C, end effector assembly 100, as noted above, includes first and second jaw members 110, 120. Each jaw member 110, 120 includes a proximal flange portion 111, 121, an outer insulative jaw housing 112, 122 disposed about the distal portion (not explicitly shown) of each jaw member 110, 120, and a tissue-contacting surface 114, 124, respectively. Proximal flange portions 111, 121 are pivotably coupled to one another about pivot 103 for moving jaw members 110, 120 between the spaced-apart and approximated positions, although other suitable mechanisms for pivoting jaw members 110, 120 relative to one another are also contemplated. The distal portions (not explicitly shown) of the jaw members 110, 120 are configured to support jaw housings 112, 122, and tissue-contacting surfaces 114, 124, respectively, thereon.

Outer insulative jaw housings 112, 122 of jaw members 110, 120 support and retain tissue-contacting surfaces 114, 124 on respective jaw members 110, 120 in opposed relation relative to one another. Tissue-contacting surfaces 114, 124 are at least partially formed from an electrically conductive material, e.g., for conducting electrical energy therebetween for treating tissue, although tissue-contacting surfaces 114, 124 may alternatively be configured to conduct any suitable energy, e.g., thermal, microwave, light, ultrasonic, etc., through tissue grasped therebetween for energy-based tissue treatment. As mentioned above, tissue-contacting surfaces 114, 124 are coupled to activation switch 80 and electrosurgical generator 400, e.g., via the wires (not shown) extending from cable 90 through forceps 10, such that energy may be selectively supplied to tissue-contacting surface 114 and/or tissue-contacting surface 124 and conducted therebetween and through tissue disposed between jaw members 110, 120 to treat tissue.

Continuing with reference to FIGS. 1B and 1C, end effector assembly 100 further includes a sensor mechanism 150 including components disposed within, on, or otherwise associated with one or both of jaw members 110, 120. Sensor mechanism 150 is configured to sense one or more properties of smoke and/or steam between jaw members 110, 120 and/or in the surrounding environment and to provide sensor feedback to generator 400 (FIG. 1) to detect, analyze, and/or distinguish smoke during the application of energy to tissue, after the application of energy to tissue, and/or intermittently between energy application, e.g., to determine one or more parameters thereof. Various configurations of sensor mechanism 150 are detailed below.

With reference to FIGS. 2A-2D, a multi-function surgical instrument provided in accordance with the present disclosure is shown generally identified by reference numeral 210. Instrument 210 includes similar features as forceps 10 (FIGS. 1A-1C) except that instrument 210 further includes a second activation assembly 270, a deployable assembly 280, and a deployment and retraction mechanism 290 and, thus, only these additional features are detailed below.

Deployable assembly 280 includes a sheath 282 and an energizable member 284. Sheath 282, in embodiments, is insulative, although other configurations are also contemplated. Sheath 282 is movable relative to end effector assembly 100' between a retracted position, wherein sheath 282 is disposed proximally of end effector assembly 100', and an extended position, wherein sheath 282 is substantially disposed about end effector assembly 100'. Energizable member 284 is coupled to generator 400 (FIG. 1A) and second activation assembly 270 via one or more wires (not shown) and may function as the active electrode of a monopolar circuit or may be energizable with any other suitable form of energy, e.g., thermal, microwave, etc. Energizable member 284 is movable together with sheath 282 and relative to end effector assembly 100' between a retracted position, wherein distal tissue-treating portion 286 of energizable member 284 is positioned more-proximally, and an extended position, wherein distal tissue-treating portion 286 of energizable member 284 extends distally from end effector assembly 100' to facilitate treating tissue therewith. Energizable member 284, more specifically, is engaged with sleeve 282 such that energizable member 284 and sleeve 282 move together between their respective retracted and extended positions (collectively the retracted and extended positions of deployable assembly 280). In the extended position, in embodiments where sheath 282 is insulative, sheath 282 serves to electrically insulate end effector assembly 100' from distal tissue-treating portion 286 of energizable member 284, while distal tissue-treating portion 286 extends distally from end effector assembly 100'. In the extended position, energy may be supplied to distal tissue-treating portion 286 of energizable member 284, e.g., via activation of either of the activation switches 272 of second activation assembly 270, for treating, e.g., dissecting, tissue.

Deployment and retraction mechanism 290 is configured for selectively transitioning deployable assembly 280 between its retracted position and its extended position. Deployment and retraction mechanism 290 generally includes a gear assembly (not shown) disposed within housing 220, a pair of input shafts 292 operably coupled to the gear assembly and extending transversely from either side of housing 220, a pair of deployment paddles 294 operably coupled to the input shafts 292 (only one side of housing 220 and, thus, one paddle 294 is illustrated), and a slider (not shown) disposed within housing 220 and operably coupling an output of the gear assembly with energizable member 284 of deployable assembly 280 (which, in turn, is engaged with sheath 282) such that deployment and retraction mechanism 290 is configured to enable both deployment and retraction of deployable assembly 280 in a push-push manner, e.g., wherein deployable assembly 280 is both deployed and retracted by pushing either of paddles 294 in the same direction. Other configurations are also contemplated. Further, as opposed to a multi-function instrument, an instrument including just an energizable member 284 of any suitable configuration and/or energy (monopolar, bipolar, thermal, etc.) is also contemplated.

Figure 3:
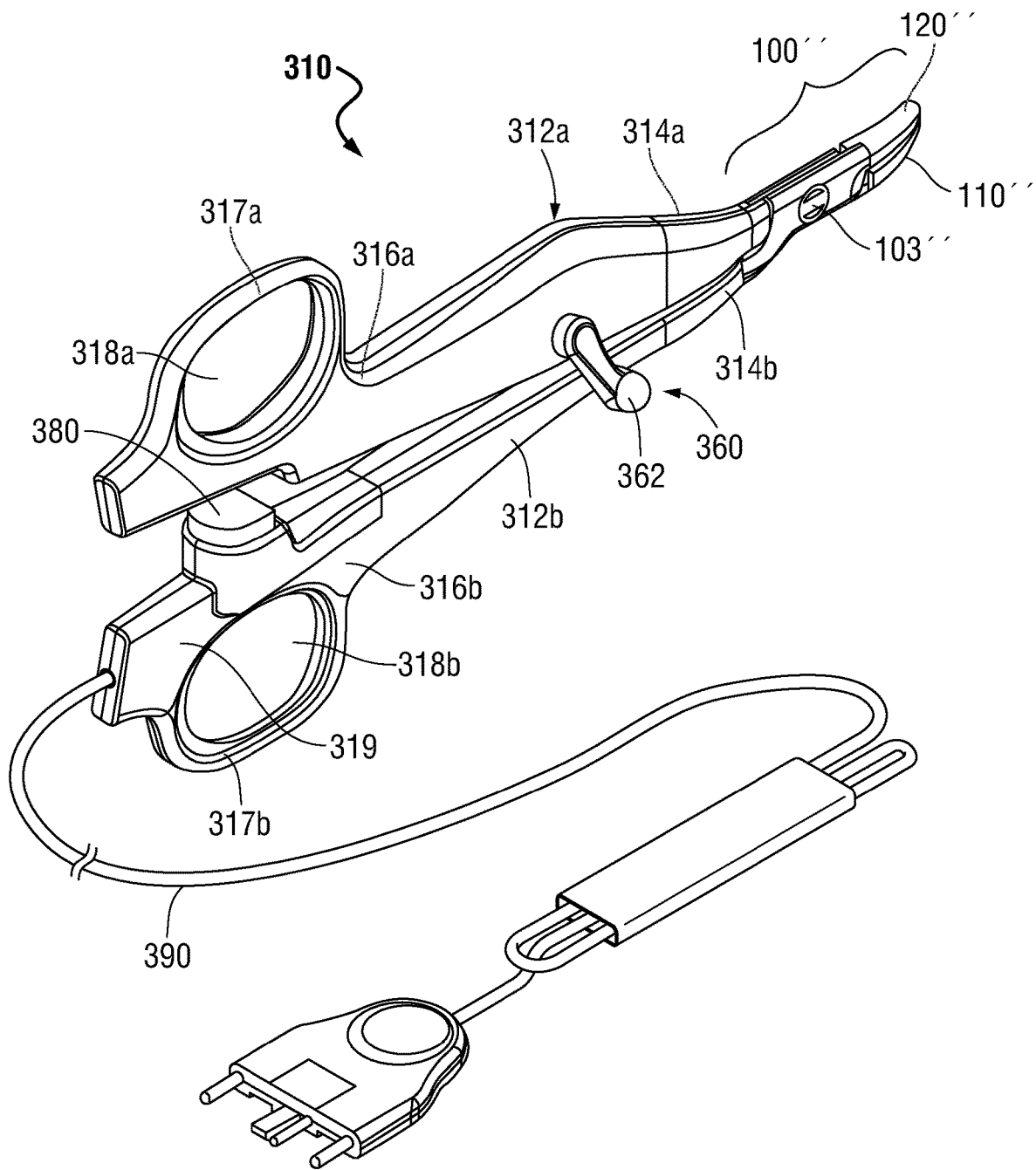
FIG. 3 is a perspective view of a hemostat-style electrosurgical forceps provided in accordance with the present disclosure.

Referring to FIG. 3, a hemostat-style electrosurgical forceps provided in accordance with the present disclosure is shown generally identified by reference numeral 310. Aspects and features of forceps 310 not germane to the understanding of the present disclosure are omitted to avoid obscuring the aspects and features of the present disclosure in unnecessary detail.

Forceps 310 includes two elongated shaft members 312a, 312b, each having a proximal end portion 316a, 316b, and a distal end portion 314a, 314b, respectively. Forceps 310 is configured for use with an end effector assembly 100" similar to end effector assembly 100 (FIGS. 1B and 1C). More specifically, end effector assembly 100" includes first and second jaw members 110", 120" attached to respective distal end portions 314a, 314b of shaft members 312a, 312b. Jaw members 110", 120" are pivotably connected about a pivot 103". Each shaft member 312a, 312b includes a handle 317a, 317b disposed at the proximal end portion 316a, 316b thereof. Each handle 317a, 317b defines a finger hole 318a, 318b therethrough for receiving a finger of the user. As can be appreciated, finger holes 318a, 318b facilitate movement of the shaft members 312a, 312b relative to one another to, in turn, pivot jaw members 110", 120" from the spaced-apart position, wherein jaw members 110", 120" are disposed in spaced relation relative to one another, to the approximated position, wherein jaw members 110", 120" cooperate to grasp tissue therebetween.

One of the shaft members 312a, 312b of forceps 310, e.g., shaft member 312b, includes a proximal shaft connector 319 configured to connect forceps 310 to electrosurgical generator 400 (FIG. 1A). Proximal shaft connector 319 secures a cable 390 to forceps 310 such that the user may selectively supply energy to jaw members 110", 120" for treating tissue. More specifically, an activation switch 380 is provided for supplying energy to jaw members 110", 120" to treat tissue upon sufficient approximation of shaft members 312a, 312b, e.g., upon activation of activation switch 380 via shaft member 312a.

Forceps 310 further includes a trigger assembly 360 including a trigger 362 coupled to one of the shaft members, e.g., shaft member 312a, and movable relative thereto between an un-actuated position and an actuated position. Trigger 362 is operably coupled to a knife (not shown; similar to knife 64 (FIG. 1B) of forceps 10 (FIG. 1A)) so as to actuate the knife to cut tissue grasped between jaw members 110", 120" of end effector assembly 100" upon movement of trigger 362 to the actuated position. Similarly as noted above with respect to forceps 10 (FIG. 1A), other suitable cutting mechanisms are also contemplated.

Figure 4:
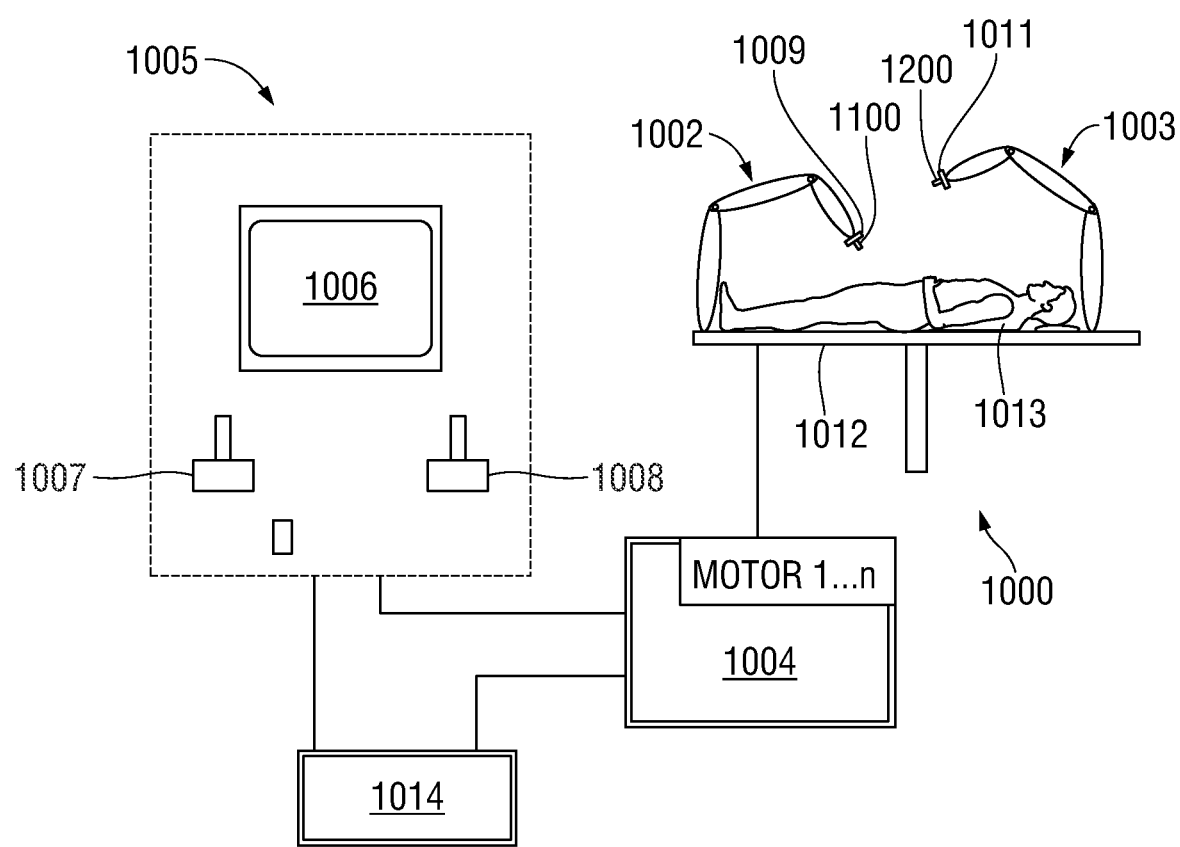
FIG. 4 is a schematic illustration of a robotic surgical instrument provided in accordance with the present disclosure.

Referring to FIG. 4, a robotic surgical instrument provided in accordance with the present disclosure is shown generally identified by reference numeral 1000. Aspects and features of robotic surgical instrument 1000 not germane to the understanding of the present disclosure are omitted to avoid obscuring the aspects and features of the present disclosure in unnecessary detail.

Robotic surgical instrument 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in a first operating mode. Robotic surgical instrument 1000 may be configured for use on a patient 1013 lying on a patient table 1012 to be treated in a minimally invasive manner. Robotic surgical instrument 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 is similar to end effector assembly 100 (FIGS. 1B and 1C), although other suitable end effector assemblies for coupling to attaching device 1009 are also contemplated. End effector assembly 1100 is connected to electrosurgical generator 400 (FIG. 1A), which may be integrated into or separate from robotic surgical instrument 1000. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Figure 5:
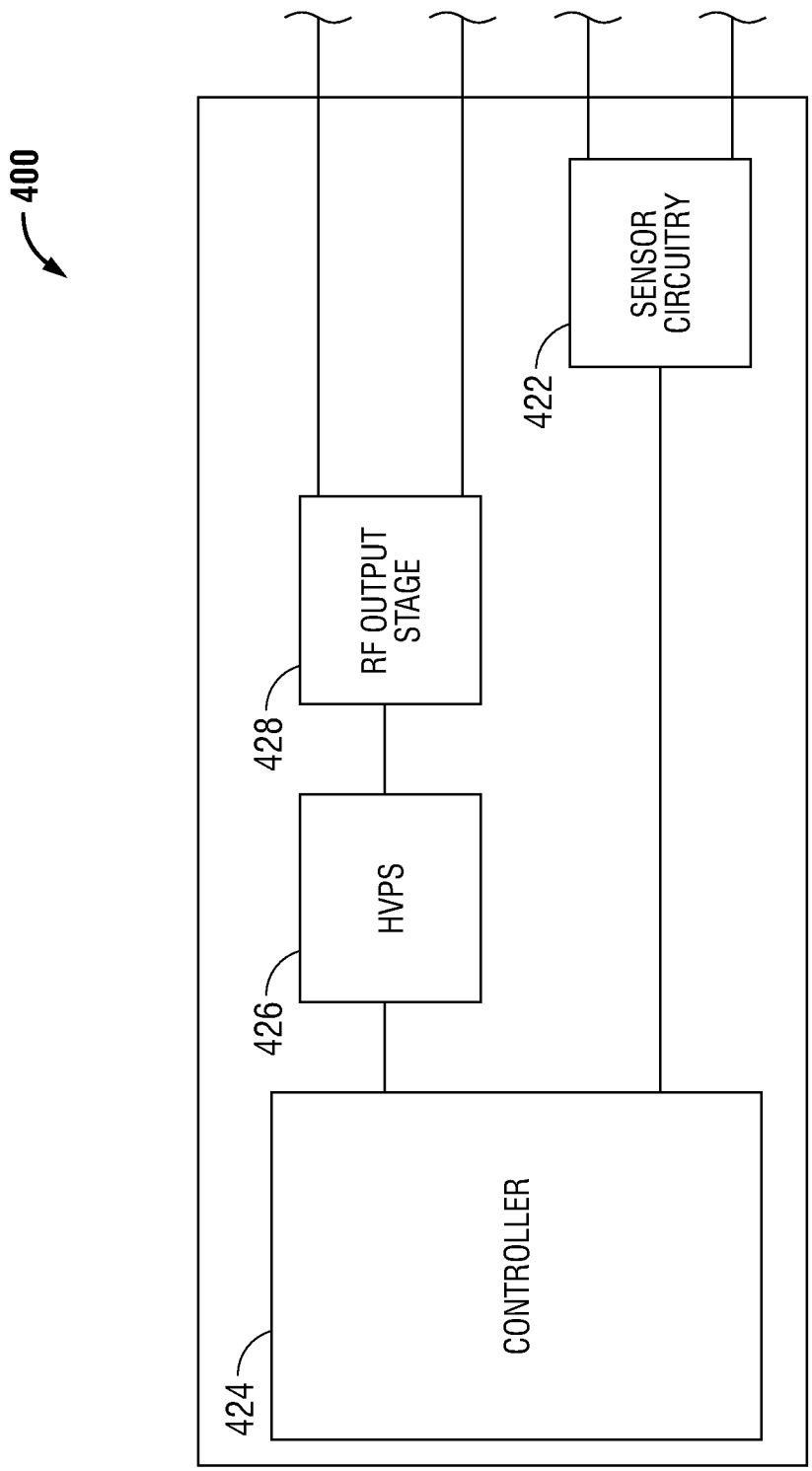
FIG. 5 is a block diagram of the electrosurgical generator of FIG. 1.

Referring to FIG. 5, electrosurgical generator 400 is shown as a schematic block diagram. Generator 400 may be utilized as a stand-alone generator (as shown in FIG. 1A), may be incorporated into a surgical instrument 10, 210, 1000 (FIGS. 1, 3, and 4, respectively), or may be provided in any other suitable manner. Generator 400 includes sensor circuitry 422, a controller 424, a high voltage DC power supply ("HVPS") 426 and an RF output stage 428. Sensor circuitry 422 is configured to receive sensor feedback from sensor mechanism 150 (FIGS. 1B and 1C) and to relay the same to controller 424. Controller 424 is configured to control the output of energy from HVPS 426 to RF output stage 428 and, thus, the application of energy from tissue-contacting surfaces 114, 124 of jaw members 110, 120 to tissue grasped therebetween (FIGS. 1B and 1C). More specifically, controller 424 is configured to receive the sensor feedback from sensor circuitry 422; detect, analyze, and/or distinguish smoke and steam in real time during the application of energy to tissue (FIGS. 1B and 1C); and, based thereon, start, continue, modify, stop, etc., the output of energy from HVPS 426 to RF output stage 428. Alternatively or additionally, controller 424 may provide a suitable output, e.g., an audible, visual, and/or tactile indicator, to the user based upon the smoke and steam detected, analyzed, and/or distinguished. Controller 424 is detailed below.

HVPS 426, under the direction of controller 424, provides high voltage DC power to RF output stage 428 which converts the high voltage DC power into RF energy for delivery to tissue-contacting 114, 124 of jaw members 110, 120, respectively, of end effector assembly 100 (see FIGS. 1B and 1C). In particular, RF output stage 428 generates sinusoidal waveforms of high frequency RF energy. RF output stage 428 may be configured to generate waveforms having various duty cycles, peak voltages, crest factors, and other properties. Other suitable configurations are also contemplated such as for example, pulsed energy output, other waveforms, etc.

Figure 6:
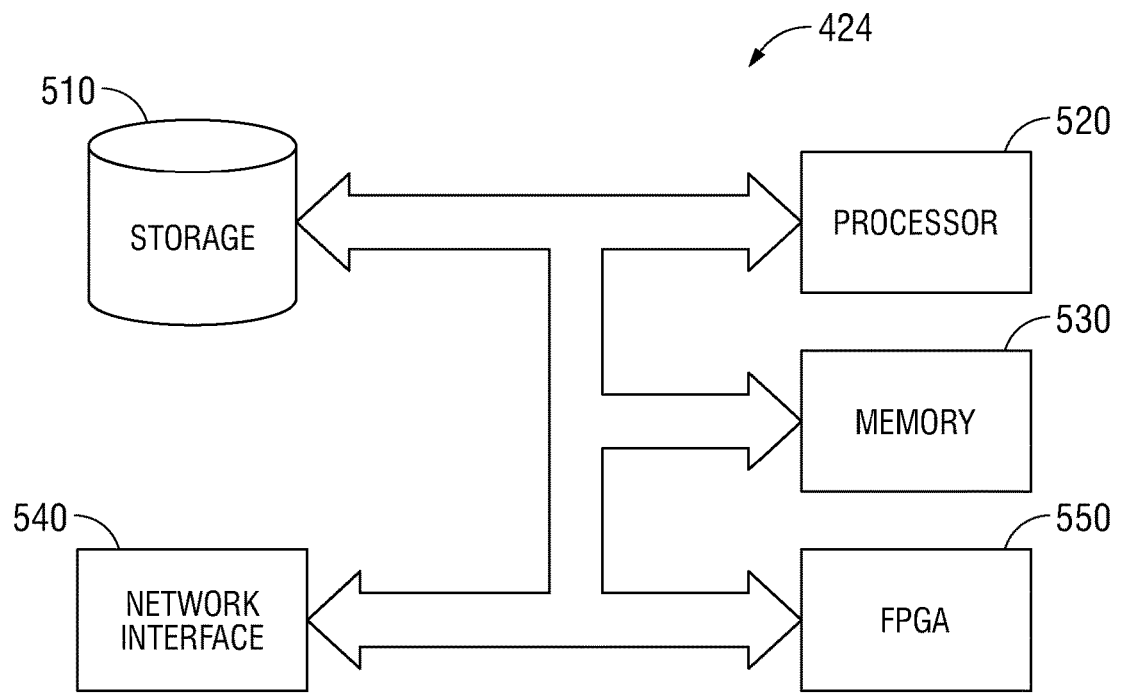
FIG. 6 is a block diagram of a controller of the electrosurgical generator of FIG. 5.

With additional reference to FIG. 6, controller 424 is configured to receive the sensor feedback from sensor circuitry 422 (as sensed by sensor mechanism 150 (FIGS. 1B and 1C)) and, based thereon, detect, analyze, and/or distinguish smoke and steam in real-time (allowing computer processing time within a suitable real-time constraint), before, during, after, and/or intermittently between the application of energy to the tissue. The detection, analysis, and/or distinction of smoke and steam may include determining one or more parameters of smoke and/or steam, for example: determining the presence, relative amount, constituency, density, spread, etc. of smoke; and/or determining the presence, relative amount, temperature, density, spread, etc. of steam. This detection, analysis, and/or distinction may be accomplished using, for example, a look-up table correlating the sensor feedback with the one or more parameters of smoke and/or steam. Alternatively, a fixed algorithm determining the one or more parameters of smoke and/or steam based upon the sensor feedback may be utilized. As another alternative, the one or more parameters of smoke and/or steam may be determined using a machine learning algorithm. This detection, analysis, and/or distinction may additionally or alternatively be utilized for minimizing smoke and/or steam generation.

Referring particularly to FIG. 6, controller 424 includes a processor 520 connected to a computer-readable storage medium or a memory 530 which may be a volatile type memory, e.g., RAM, or a non-volatile type memory, e.g., flash media, disk media, etc. In embodiments, processor 520 may be, without limitation, a digital signal processor, a microprocessor, an ASIC, a graphics processing unit (GPU), field-programmable gate array (FPGA), or a central processing unit (CPU). In embodiments, memory 530 can be random access memory, read-only memory, magnetic disk memory, solid state memory, optical disc memory, and/or another type of memory. In embodiments, memory 530 can be separate from controller 424 and can communicate with processor 520 through communication buses of a circuit board and/or through communication cables such as serial ATA cables or other types of cables. Memory 530 includes computer-readable instructions that are executable by processor 520 to operate controller 424. In embodiments, controller 424 includes a network interface 540 to communicate with other computers or a server. In embodiments, a storage device 510 may be used for storing data. In embodiments, controller 424 may include one or more FPGAs 550. FPGA 550 may be used for executing various algorithms, e.g., fixed algorithms, machine learning algorithms, etc.

Memory 530 stores suitable instructions, to be executed by processor 520, for receiving the sensed data, e.g., sensed data from sensor circuitry 422 (FIG. 5), accessing storage device 510 of controller 424, and determining the one or more parameters of smoke and/or steam based upon the sensed data and information stored in storage device 510. Memory 530 further stores suitable instructions, to be executed by processor 520, to provide feedback based upon the one or more parameters of smoke and/or steam. Although illustrated as part of generator 400, it is also contemplated that controller 424 be remote from generator 400, e.g., on a remote server, and accessible by generator 400 via a wired or wireless connection. In embodiments where controller 424 is remote, it is contemplated that controller 424 may be accessible by and connected to multiple generators 400.

Figure 7:
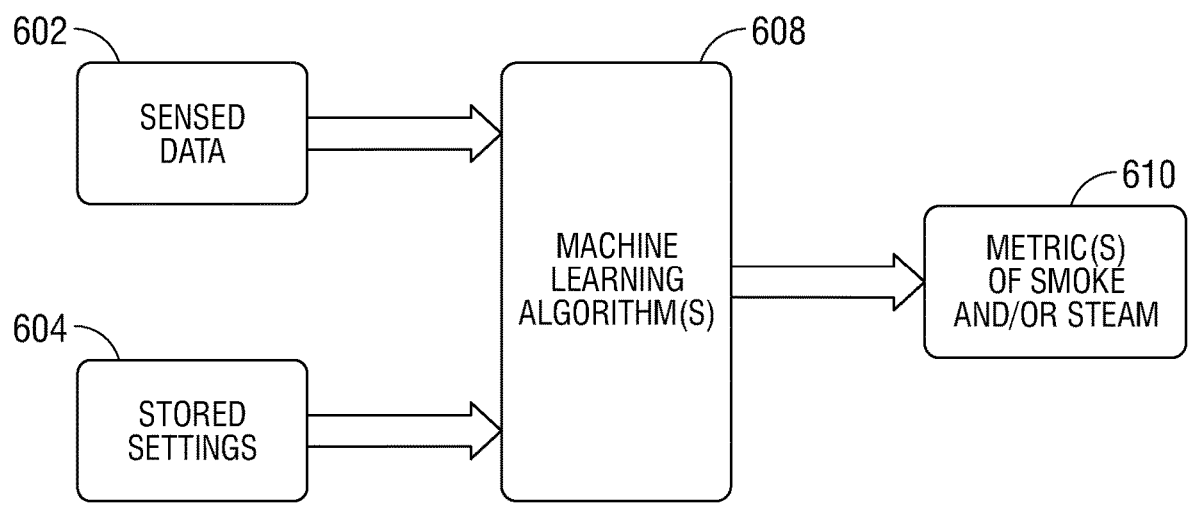
FIG. 7 is a logic diagram of a machine learning algorithm in accordance with the present disclosure.

With reference to FIGS. 6 and 7, in embodiments where one or more machine learning machine learning algorithms 608 are used, storage device 510 of controller 424 stores the one or more machine learning algorithms 608. The machine learning algorithm(s) 608 may be trained on and learn from stored settings 604, e.g., experimental data and/or data from previous procedures initially input into the one or more machine learning applications, and/or the sensed data 602 from sensor circuitry 422 (FIG. 5) in order to enable the machine learning application(s) to determine the one or more parameters of smoke and/or steam 610. In embodiments, training the machine learning algorithm may be performed by a computing device outside of generator 400 and the resulting algorithm may be communicated to controller 424 of generator 400.

In embodiments, controller 424 receives the determined one or more parameters of smoke and/or steam 610 that was output from the machine learning algorithm 608 and communicates the same to a computing device, e.g., of controller 424, for use in controlling the output of energy from HVPS 426 to RF output stage 428. This controlling may include starting, continuing, modifying, or stopping the output of energy. More specifically, a tissue treating algorithm stored in storage device 510 of controller 424 may be implemented, modified, stopped, switched to another tissue treating algorithm, etc.; the waveform output may modified, stopped, switched to another tissue treating waveform; a setting may be changed, e.g., power may be increased or decreased; and/or an energy output time may be increased or decreased. That is, the energy output is adapted, if necessary, in accordance with the one or more parameters of smoke and/or steam determined. In this manner, smoke and/or steam may be monitored during tissue treatment, e.g., tissue sealing, to ensure that the desired tissue treatment is achieved, e.g., sealing the tissue, and, after, to check that a sufficient tissue effect, e.g., a tissue seal, indeed resulted.

For example, the parameter(s): the presence of smoke; the presence of a particular type of smoke particle or particles; the amount of smoke particles or relative ratio of different smoke particles; a ratio of smoke (or particles thereof) to steam (measured in particles, volume, etc.) exceeding a threshold; the temperature, density, color (or other optical parameter) of smoke; and/or the extent of smoke spread may indicate, during the application of energy to tissue to treat, e.g., seal, tissue, a status of the tissue sealing process, e.g., whether collagen has denatured, liquefied, and crosslinked, whether the tissue is being burned, whether collateral tissue is being burned, etc., since smoke and/or steam generated may vary during the various stages of tissue sealing and/or as a result of different effects on tissue. The energy applied may then be varied, if appropriate, in accordance with the status of the tissue sealing process in order to facilitate tissue sealing and/or reduce collateral damage.

As another example, the above parameters may indicate a type of tissue, e.g., vascular, muscle, organ, etc., and/or a state of tissue, e.g., healthy, diseased, etc., during the application of energy to tissue to treat, e.g., seal, tissue, as smoke and/or steam may be generated differently based upon the type and/or state of tissue to which the energy is applied. The energy-delivery algorithm may then be varied, if appropriate, in order to facilitate treatment of the particular tissue type and/or state determined.

As noted above, controller 424 may alternatively or additionally receive the determined one or more parameters of smoke and/or steam 610 that was output from the machine learning algorithm 608 and communicate the same to a computing device, e.g., of controller 424, for use in providing a suitable output, e.g., an audible, visual, and/or tactile indicator, to the user based upon the one or more parameters of smoke and/or steam 610.

For example, the parameter(s): the presence of smoke; the presence of a particular type of smoke particle or particles; the amount of smoke particles or relative ratio of different smoke particles; a ratio of smoke (or particles thereof) to steam (measured in particles, volume, etc.) exceeding a threshold; the temperature, density, color (or other optical parameter) of smoke; and/or the extent of smoke spread may indicate, during the application of energy to tissue to treat, e.g., seal, tissue, a state of tissue, e.g., healthy, diseased (cancerous), etc. Accordingly, with respect to a diseased tissue removal procedure, a suitable output may be provided to the user to indicate to the user that the tissue being treated is diseased. This may allow the user, for example, to further remove tissue until the margins are not diseased (and no such output is given). Thus, the output facilitates the full removal of diseased tissue by helping to identify the margins of the diseased tissue.

As another example, the above parameters may indicate a type of tissue, e.g., vascular, muscle, organ, etc., and/or the presence of a foreign object or a critical tissue, e.g., nerve, organ, duct, etc. during the application of energy to tissue to treat, e.g., seal, tissue, as smoke and/or steam may be generated differently based upon the type of tissue to which the energy is applied and/or based upon surrounding objects, critical tissue, etc. Accordingly, a suitable output may be provided to the user to indicate to the user a type of tissue and/or the presence of a foreign object or a critical tissue that the user may be unaware of, thus helping to prevent inadvertent treatment. The application of energy to tissue may also be automatically stopped or paused based upon the detection of a particular type of tissue, a foreign object, or a critical tissue (together with the output or separate therefrom), providing a further safety feature against inadvertent treatment.

Turning to FIGS. 8-10B, detailed below are various embodiments of sensor mechanisms 150 incorporated into or associated with jaw member 110 and/or jaw member 120 of end effector assembly 100 (or any other end effector assembly detailed herein or suitable for use in accordance with the present disclosure). As noted above, sensor mechanisms 150 are configured to communicate sensor feedback to sensor circuitry 422 of generator 400 (see FIG. 5) which, in turn, is configured to communicate with controller 424 (see FIG. 6) to enable the detection, analysis, and/or distinction of smoke and steam in real-time during the application of energy to tissue.

Referring initially to FIG. 8, in embodiments, sensor mechanism 150 may include one or more sensor assemblies 730 positioned within knife channels 116, 126 defined within the first and second jaw members 110, 120. The one or more sensor assemblies 730 may include one or more transmitters, e.g., a transmitter 732 disposed within knife channel 116 of jaw member 110, one or more receivers, e.g., a receiver 734 disposed within knife channel 126 of jaw member 120, and/or one or more transceivers (not shown) configured to cooperate to sense one or more properties of smoke and/or steam within tissue "T" and/or the surrounding environment, e.g., disposed within knife channels 116, 126, and to provide the same to sensor circuitry 422 (FIG. 5) for determination of the one or more parameters of smoke and/or steam.

In embodiments, sensor assembly 730 is an optical sensor assembly utilizing fluorescence spectroscopy, infrared imaging, video imaging, or other suitable optical technique to sense one or more optical properties of smoke and/or steam within tissue "T" and/or the surrounding environment. In other embodiments, sensor assembly 730 is a smoke and/or other particle detector, e.g., an ionization detector or a photoelectric detector, and is configured to detect smoke and/or other particles within the surrounding environment. In still other embodiments, the sensor assembly 730 is an electronic nose configured to electronically sense one or more smell-based properties of smoke and/or steam within tissue "T" and/or the surrounding environment. In yet another embodiment, the sensor assembly 730 is a chemical sensor, e.g., a molecular sensor, gas chromatograph, etc., configured to sense one or more chemical properties of smoke and/or steam within tissue "T" and/or the surrounding environment. Other suitable sensors including but not limited to, for example, moisture sensors, pressure sensors, density sensors, temperature sensors, ultrasonic sensors, audio sensors, etc., are also contemplated. Further, combinations of sensors, e.g., two or more of the above-noted or other suitable sensors, may be utilized.

Regardless of the particular sensor configuration utilized, the sensed properties, as noted above, are used to determine one or more parameters such as, for example, the presence of smoke; the presence of a particular type of smoke particle or particles; the amount of smoke particles or relative ratio of different smoke particles; a ratio of smoke (or particles thereof) to steam (measured in particles, volume, etc.) exceeding a threshold; the temperature, density, color (or other optical parameter) of smoke; and/or the extent of smoke spread.

As an alternative to positioning sensor assembly 730, e.g., transmitters 732, receivers 734, and/or transceivers (not shown), within one or both of knife channels 116, 126 of first and second jaw members 110, 120, respectively, the components 732, 734 of sensor assembly 730 may be disposed at any other suitable position on or within jaw member 110 and/or jaw member 120. For example, sensor mechanism 150 may alternatively or additionally include one or more tissue-surface sensors (not shown) configured to contact a surface of tissue "T" grasped between jaw members 110, 120.

With reference to FIG. 9, sensor mechanism 150, in embodiments, may be associated with a device 740 external to and, in embodiments, independent of, end effector assembly 100. Device 740 may be, for example, an endoscopic camera including a sensor assembly 742 including one or more optical sensors 744 such as those detailed above. Alternatively, device 740 may be a surgical probe or other suitable device carrying one or more other sensors, e.g., any of the sensors detailed above. The sensor assembly, e.g., sensor assembly 742, is configured to sense one or more properties of smoke and/or steam within tissue "T" and/or the surrounding environment, e.g., the volume surrounding end effector assembly 100, and to provide the same to sensor circuitry 422 (FIG. 5). In embodiments, device 740 may include a visible light and/or infrared camera to enable sensing of thermal spread, tissue expansion, tissue color, tissue temperature, etc., additionally or alternatively with the sensing of smoke and/or steam. Such sensed properties from device 740 may also be utilized to determine tissue type.

Referring to FIGS. 10A and 10B, sensor mechanism 150 may alternatively or additionally include one or more tissue-penetrating needles 750 operably coupled to a sensor assembly 752. Needles 750 protrude from jaw member 110 and/or jaw member 120 towards the other and are configured to penetrate tissue "T" grasped between jaw members 110, 120. Tissue-penetrating needles 750 may include or be associated with sensor assembly 752 including any suitable sensor(s) such as those detailed above. The sensor(s) of sensor assembly 752 are configured to sense one or more properties of the smoke and/or steam within the penetrated tissue "T" or the interior thereof. In embodiments, needles 750 may be configured to sense the smoke and/or steam within tissue "T" and/or to extract fluid, tissue, etc., from the penetrated tissue "T" to enable isolated sensing of smoke and/or steam therein. Regardless of the particular configuration of needles 750, needles 750 and sensor assembly 752 sense one or more properties to determination of one or more parameters such as, for example, the presence of smoke; the presence of a particular type of smoke particle or particles; the amount of smoke particles or relative ratio of different smoke particles; a ratio of smoke (or particles thereof) to steam (measured in particles, volume, etc.) exceeding a threshold; the temperature, density, color (or other optical parameter) of smoke; and/or the extent of smoke spread.

Figure 11:
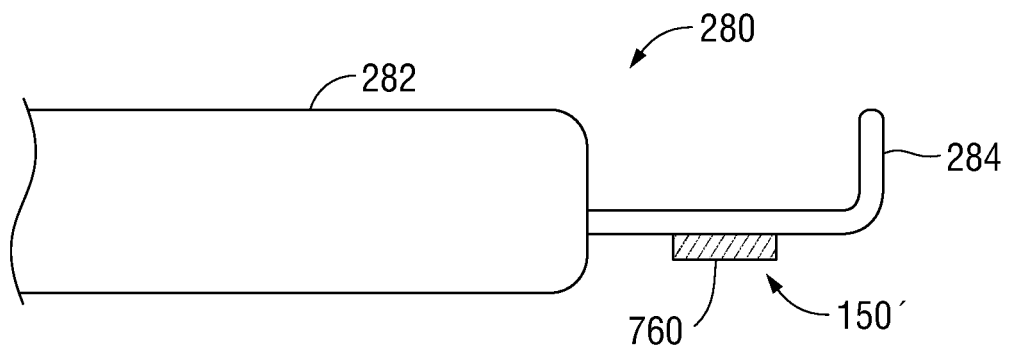
FIGS. 11-13 are side views of a distal portion of the shaft-based multi-function instrument of FIG. 2A with the deployable assembly thereof disposed in an extended position and various sensor mechanisms incorporated therein or associated therewith.
Figure 12:
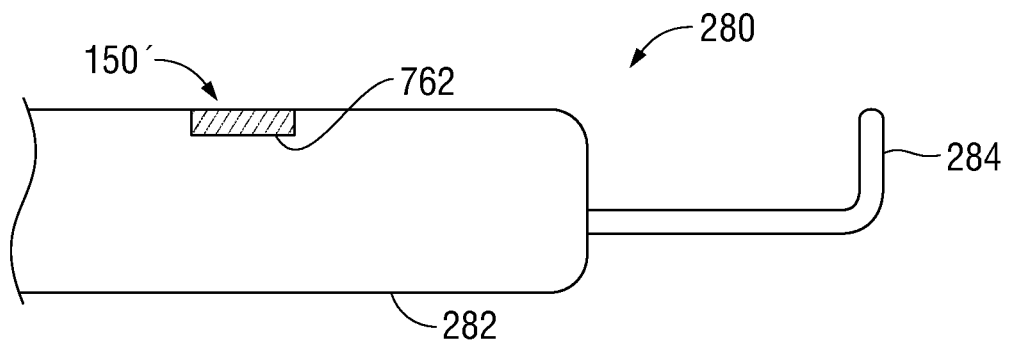
Figure 13:
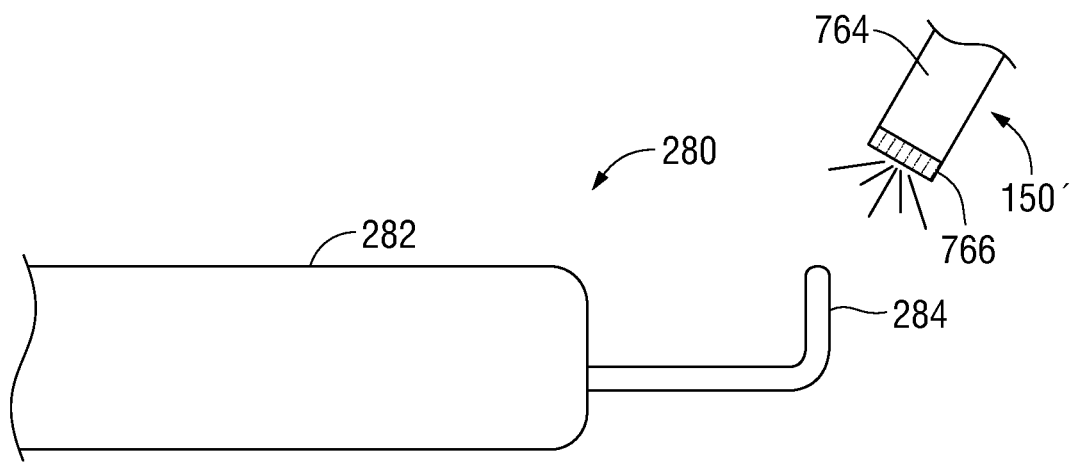

Turning to FIGS. 11-13, various embodiments of sensor mechanisms 150' incorporated into or associated within deployable assembly 280 of surgical instrument 210, although sensor mechanisms 150' may alternatively by incorporated into any other suitable surgical instrument, e.g., an electrosurgical probe or other energy-based device, an access device, a tissue manipulation device, a visualization device, a dedicated sensing device, etc. Referring to FIG. 11, sensor mechanism 150' may include a sensor assembly 760 disposed on energizable member 284. Sensor assembly 760 may include any suitable sensor, e.g., any of the sensors detailed above, and is configured to sense one or more properties of smoke and/or steam within tissue adjacent deployable assembly 280 and/or the surrounding environment, e.g., the volume surrounding deployable assembly 280, and to provide the same to sensor circuitry 422 (FIG. 5) for determination of the one or more parameters of smoke and/or steam.

As shown in FIG. 12, sensor mechanism 150' may include a sensor assembly 762 disposed within sheath 282 of deployable assembly 280. Sensor assembly 762 may include any suitable sensor, e.g., any of the sensors detailed above, and is configured to sense one or more properties of smoke and/or steam within sheath 282, and to provide the same to sensor circuitry 422 (FIG. 5) for determination of the one or more parameters of smoke and/or steam.

FIG. 13 illustrates a configuration wherein sensor mechanism 150' is associated with a device 764 external to and, in embodiments, independent of, deployable assembly 280. Device 764 includes one or more sensors 766, may be similar to any of the embodiments of device 740 (FIG. 9) detailed above, and is configured to sense one or more properties of smoke and/or steam within tissue adjacent deployable assembly 280 and/or the surrounding environment, and to provide the same to sensor circuitry 422 (FIG. 5) for determination of the one or more parameters of smoke and/or steam.

In any of the above-detailed embodiments of sensor mechanism 150 and/or sensor mechanism 150', suction may be incorporated into the instrument via one or more suction channels, apertures, etc. connected to a suction source (not shown) to direct, e.g., draw, fluid to the sensor assemblies to facilitate determination of the one or more parameters of smoke and/or steam. In such embodiments, the sensor mechanisms 150, 150' may be more-proximally disposed such as within the shaft or housing, whereby the fluid travels through a suction conduit to the sensor mechanism 150, 150' for determination of the one or more parameters of smoke and/or steam.

It should be understood that various aspects disclosed herein may be combined in different combinations than the combinations specifically presented hereinabove and in the accompanying drawings. In addition, while certain aspects of the present disclosure are described as being performed by a single module or unit for purposes of clarity, it should be understood that the techniques of this disclosure may be performed by a combination of units or modules associated with, for example, a surgical system.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structures or any other physical structure suitable for implementation of the described techniques. Also, the techniques could be fully implemented in one or more circuits or logic elements.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
   an end effector assembly including first and second jaw members each defining an electrically-conductive tissue-contacting surface, at least one of the first or second jaw members movable relative to the other between a spaced-apart position and an approximated position for grasping tissue between the tissue-contacting surfaces thereof, the electrically-conductive tissue-contacting surfaces of the first and second jaw members adapted to connect to a source of electrosurgical energy for conducting energy through tissue grasped therebetween to effect a tissue treatment;
   a sensor configured to sense at least one property indicative of a relationship between smoke and steam produced as a result of the conduction of energy through tissue grasped between the electrically-conductive tissue-contacting surfaces, wherein the sensor is incorporated into assembly a knife slot of one of the first jaw member or the second jaw member; and
   a controller configured to receive the sensed at least one property from the sensor, to determine the relationship between smoke and steam based at least in part on the sensed at least one property, to determine whether the tissue being treated with the energy has undergone collagen transformation based at least in part on the determined relationship between smoke and steam, and to control the energy conducted through tissue grasped between the electrically-conductive tissue-contacting surfaces based at least in part on the determination of whether the tissue being treated with the energy has undergone collagen transformation.

2. The electrosurgical system according to claim 1, wherein the sensor is disposed on or within one of the first or second jaw members.

3. The electrosurgical system according to claim 1, wherein the sensor includes at least one of: an optical sensor, an electrical sensor, a smell-based sensor, or a chemical sensor.

4. The electrosurgical system according to claim 1, wherein the at least one property includes: an optical property, a chemical property, an electrical property, or a smell-based property.

5. The electrosurgical system according to claim 1, wherein the sensed at least one property is indicative of a ratio of smoke to steam produced as a result of the conduction of energy through tissue grasped between the electrically-conductive tissue-contacting surfaces.

6. The electrosurgical system according to claim 1, wherein the controller is further configured to determine a type of tissue being treated based upon the at least one property.

7. The electrosurgical system according to claim 1, further comprising:
   a housing; and
   a shaft extending distally from the housing, wherein the end effector assembly is disposed at a distal end portion of the shaft.

8. The electrosurgical system according to claim 7, further comprising a manual actuator coupled to the housing and configured to move the at least one of the first or second jaw members between the spaced-apart position and the approximated position.

9. The electrosurgical system according to claim 1, further comprising:
   first and second shaft members pivotably coupled to one another about a pivot, wherein the end effector assembly extends distally from the pivot, and wherein the first and second shaft members are movable relative to one another to move the at least one of the first or second jaw members between the spaced-apart position and the approximated position.

10. The electrosurgical system according to claim 1, further comprising:
    a robotic arm, wherein the end effector assembly extends distally from the robotic arm.

11. The electrosurgical system according to claim 1, wherein the sensor is an optical sensor including a transmitter and a receiver.

12. The electrosurgical system according to claim 1, wherein the sensor includes at least one needle configured to penetrate tissue grasped between the tissue-contacting surfaces of the first and second jaw members.

13. The electrosurgical system according to claim 1, wherein the controller is configured to control the energy conducted through tissue grasped between the electrically-conductive tissue-contacting surfaces based at least in part on the determination of whether the tissue being treated with the energy has undergone collagen transformation to facilitate effecting the tissue treatment.

14. The electrosurgical system according to claim 1, wherein the controller is configured to control the energy conducted through tissue grasped between the electrically-conductive tissue-contacting surfaces based at least in part on the determination of whether the tissue being treated with the energy has undergone collagen transformation to limit collateral damage to tissue surrounding the first and second jaw members.

15. An electrosurgical system, comprising:
an end effector assembly including first and second jaw members each defining an electrically-conductive tissue-contacting surface, at least one of the first or second jaw members movable relative to the other between a spaced-apart position and an approximated position for grasping tissue between the tissue-contacting surfaces thereof, the electrically-conductive tissue-contacting surfaces of the first and second jaw members adapted to connect to a source of electrosurgical energy for conducting energy through tissue grasped therebetween to effect a tissue treatment;
a smoke sensor configured to sense at least one property indicative of a relationship between smoke and steam produced as a result of the conduction of energy through tissue grasped between the electrically-conductive tissue-contacting surfaces, wherein the smoke sensor is incorporated into a knife slot of one of the first jaw member or the second jaw member; and
a controller configured to receive the sensed at least one property from the smoke sensor, to determine the relationship between smoke and steam based at least in part on the sensed at least one property, to determine whether the tissue being treated with the energy has been burned based at least in part on the determined relationship between smoke and steam, and to control the energy conducted through tissue grasped between the electrically-conductive tissue-contacting surfaces based at least in part on the determination of whether the tissue being treated with the energy has been burned.

16. The electrosurgical system according to claim 15, wherein the controller is configured to control the energy by reducing the energy or stopping the energy when it is determined that the tissue being treated with the energy has been burned.

17. An electrosurgical system, comprising:
an end effector assembly including first and second jaw members each defining an electrically-conductive tissue-contacting surface, at least one of the first or second jaw members movable relative to the other between a spaced-apart position and an approximated position for grasping tissue between the tissue-contacting surfaces thereof, the electrically-conductive tissue-contacting surfaces of the first and second jaw members adapted to connect to a source of electrosurgical energy for conducting energy through tissue grasped therebetween to effect a tissue treatment;
a deployable assembly including an energizable member;
a sensor, incorporated into a knife slot of one of the first or second jaw members, configured to sense at least one property indicative of a relationship between smoke and steam produced as a result of the conduction of energy through tissue grasped between the electrically-conductive tissue-contacting surfaces; and
a controller configured to receive the sensed at least one property from the sensor, to determine the relationship between smoke and steam based at least in part on the sensed at least one property, to determine whether collateral tissue has been burned as a result of the tissue being treated with the energy based at least in part on the determined relationship between smoke and steam, and to control the energy conducted through tissue grasped between the electrically-conductive tissue-contacting surfaces based at least in part on the determination of whether collateral tissue has been burned as a result of the tissue being treated with the energy.

18. The electrosurgical system according to claim 17, wherein the controller is configured to control the energy by reducing the energy or stopping the energy when it is determined that collateral tissue has been burned.

* * * * *